United States Patent [19]

Kimura

[11] Patent Number: 4,994,052
[45] Date of Patent: Feb. 19, 1991

[54] DIAPER

[76] Inventor: Keiko Kimura, New-Apartment-Kunitachi, Room 101 Kita 1-9-1, Kunitachi-shi, Tokyo, Japan

[21] Appl. No.: 371,993

[22] Filed: Jun. 27, 1989

[51] Int. Cl.⁵ .............................................. A61F 5/44
[52] U.S. Cl. ................... 604/355; 604/385.1
[58] Field of Search ........ 604/317, 348, 356, 378–383, 604/385.1, 385.2, 386, 387, 389, 391, 392, 401; 601/355; 4/450; 128/451, 845, 849, 850

[56] References Cited

U.S. PATENT DOCUMENTS

| 880,389 | 2/1908 | Murray | 604/357 |
|---|---|---|---|
| 1,368,874 | 2/1971 | Zender | 4/450 |
| 2,154,332 | 4/1939 | Hirsch | 604/356 |
| 2,548,341 | 4/1951 | Bricmont | 604/378 |
| 3,424,160 | 1/1969 | Koornwinder et al. | 604/348 |
| 3,522,808 | 8/1970 | Worcester | 604/401 |
| 3,592,194 | 7/1971 | Duncan | 604/379 |
| 3,769,978 | 11/1973 | DeNight et al. | 604/386 |
| 3,828,555 | 5/1989 | Hermansson | 604/379 |
| 3,890,973 | 6/1975 | Davis et al. | 604/392 |
| 3,962,732 | 6/1976 | Mills | 4/451 |
| 4,029,101 | 6/1977 | Chesky et al. | 604/378 |
| 4,501,587 | 2/1985 | Enloe | 604/385.1 |
| 4,560,380 | 12/1985 | Tharel | 604/385.1 |
| 4,610,679 | 9/1986 | Matsushita | 604/385.1 |
| 4,753,645 | 6/1988 | Johnson | 604/378 |
| 4,886,509 | 12/1989 | Mattsson | 604/389 |

Primary Examiner—David J. Isabella
Assistant Examiner—K. Reichle
Attorney, Agent, or Firm—Hidaka and Johansen

[57] ABSTRACT

An improved diaper having a three-dimensional configuration, made substantially of soft, flexible liquid absorbing material. The diaper comprises a substantially flat, rectangular main body, a side wall integrally formed on each of opposing sides of the main body and a sink interposed between the sidewalls. The diaper may also comprise a raised part integrally formed on one end of the main body, the height thereof is higher than that of the sidewalls, and an end wall integrally formed on the other end of the main body, having substantially the same height as that of the main body, so that the sink is enclosed by the side walls, the raised part, and the end wall, whereby discharged body excretions are kept from spilling out of the diaper.

1 Claim, 6 Drawing Sheets

1

DIAPER

BACKGROUND OF THE INVENTION

1. Field of the Invention

The present invention relates to improved diapers used for care of handicapped persons, invalids, patients, elderly persons, infants, and women in menstrual periods.

2. Description of the prior art

Popular conventional diapers of this type are so-called disposable diapers which are formed substantially flat and are made of water absorbing soft paper materials. Some of such materials contain macromolecular water absorbents.

Because of the fact that a conventional diaper is made in a substantially flat form, it tends to directly contact parts of the body in the crotch area of the user when it is bent in a U-shape and applied to the crotch area. In this state, there will be no problem with a minute quantity urination. In a single urination, however, a person ordinarily discharges urine of a quantity of about 300 to 500 cc within a time period of about 10 to 20 seconds. Therefore, urine spurting out from the body of the user can directly hit the inner surface of the diaper which is attached to the crotch area of the user. Even though the diaper is made of a water absorbing material, the impetus of the discharged urine will not allow the diaper to absorb the urine sufficiently within a short period of time because of a limited water absorbing capacity of the diaper per unit time. Consequently, some quantity of the unabsorbed urine tends to go sideways after hitting the diaper, causing so called side wetting. The side wetting results in a troublesome cleaning of the gown and/or the bed linen as well as the body of the diaper user.

In the case of discharging feces to a conventional diaper, feces tend to spread between parts of the body of the diaper user and the diaper. In this case, feces can reach a waist part or even a back part close to a shoulder and can make a mess of wide areas of the body of the diaper user, resulting in a troublesome cleaning of the body, the gown and/or the bed linen.

SUMMARY OF THE INVENTION

In light of the above situation pertaining to the conventional diapers, it is an object of the present invention to provide an improved diaper which eliminates the spilling or side wetting problem of urine which has existed with the conventional diapers.

It is another object of the present invention to provide an improved diaper which eliminates the spoilage problem by feces.

In order to achieve the objects of the invention, the improved diaper of the present invention is formed in a three dimensional shape rather than a substantially flat shape of a conventional diaper.

The improved diaper is made primarily of a soft, flexible water absorbing material, which may contain macromolecular water absorbent, having side walls formed; on each side of the diaper extending in the lengthwise direction over substantially the entire length of the diaper. Conversely, the improved diaper has a sink in its center between the side walls. The improved diaper of one embodiment of the present invention is used, being bent to a U-shape, to cover the crotch area of the user in the same manner as in the case of a conventional diaper. On the other hand, the improved diaper of other embodiment of the present invention may be used without being bent in a U-shape.

The side walls of the improved diaper make contacts with the body of the user off the center of the body, and the centrally disposed sink of the diaper provides a room between the walls, thereby not making a positive contact with the discharging parts of the body. Consequently, even though there is a quantity of a urine discharge, the side walls will prevent the urine from spilling out of the diaper sideways. Any quantity of the discharged urine not having instantaneously been absorbed to the material of the diaper can be held in the sink between the side walls for a short period of time, say, several seconds after the discharge, until it is completely soaked into the material of the diaper.

Another type of the improved diaper of the present invention has a laterally extended raised part to hold the buttocks of the user thereon so that a sufficient space is provided between the anus and the surface of the diaper in which feces can remain without spreading and without spoiling the body.

DESCRIPTION OF THE PREFERRED EMBODIMENTS

Next, the embodiments of the present invention will be described in detail.

Figure 1:
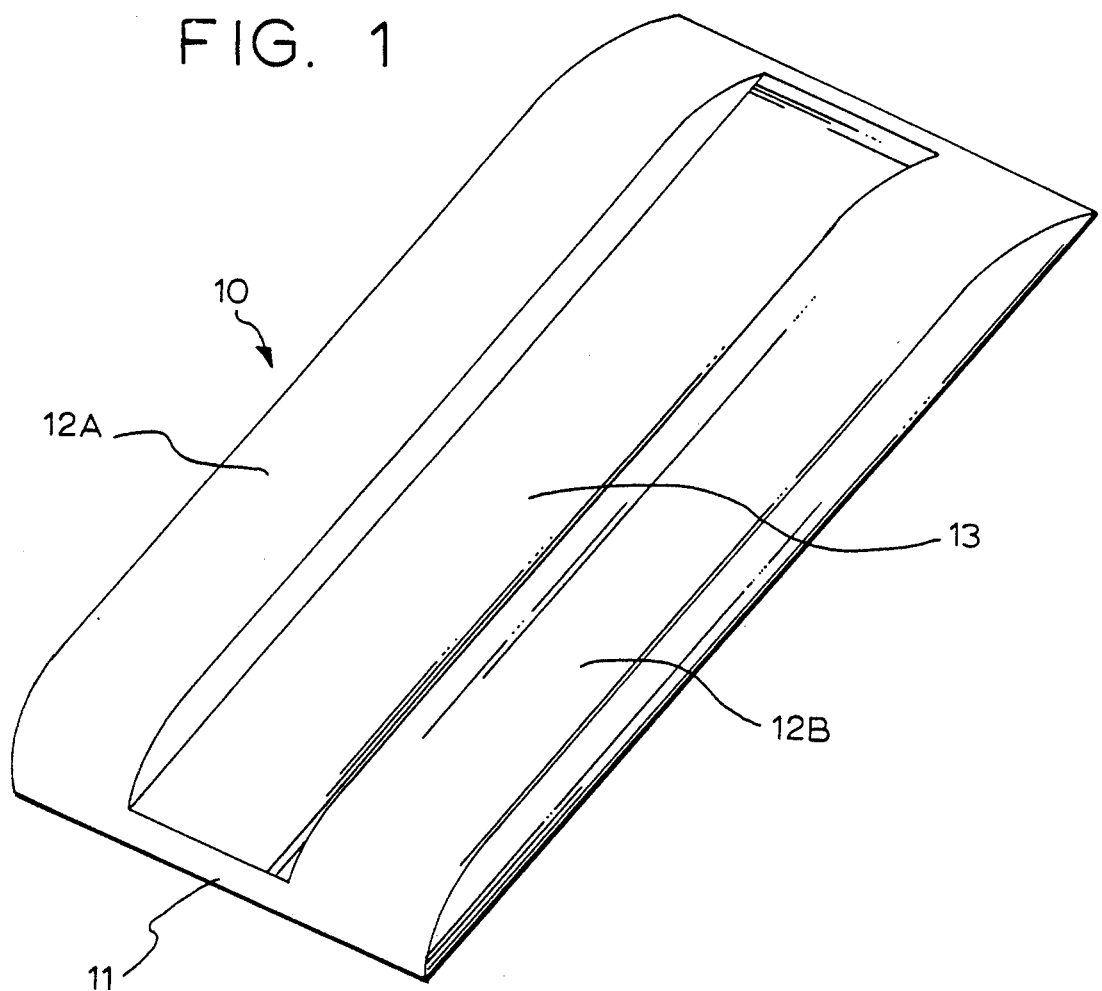
FIG. 1 is a perspective view of an improved diaper which is the first embodiment of the present invention.

FIG. 1 shows an improved diaper 10 which is the first embodiment of the present invention. In FIG. 1, numeral 11 denotes a main body of the diaper 10 made of a conventional soft, flexible paper material which may contain macromolecular water absorbent. Proper dimensions of the main body 11 are, for an adult person, about 10 to 15cm in width, about 30 to 40 cm in length and and 0.5 to 1.0 cm in thickness. The diaper 10 has a side wall 12A or 12B on each side of the inside surface of the main body 11 extending in the lengthwise direction over substantially the entire length of the diaper 10. The diaper 10 also has a sink 13 formed between the side walls 12A, 12B and extending over substantially the entire length of the diaper. The side walls 12A, 12B are formed integrally with the main body 11 of the diaper 10 and are made of the same water absorbing material as of the main body 11. The material of the side walls 12A, 12B, however, need not be limited to the same material as of the main body 11.

Proper dimensions of each of the side walls 12A, 12B, corresponding to the above described dimensions of the main body 11, are about 3 to 5 cm in width and about 1 to 2 cm in thickness. The length of the side walls 12A, 12B desirably covers the entire length of the main body 11. The end sections of the side walls 12A, 12B may be formed progressively thinner toward the respective ends of the diaper 10 as shown in FIG. 1.

When required, the side walls 12A, 12B may be formed on the left and the right sides of the main body 11 but only in a longitudinally middle section thereof.

The diaper as described above can also be used for babies, infants and for women in menstrual periods by properly reducing its dimensions.

Figure 2:
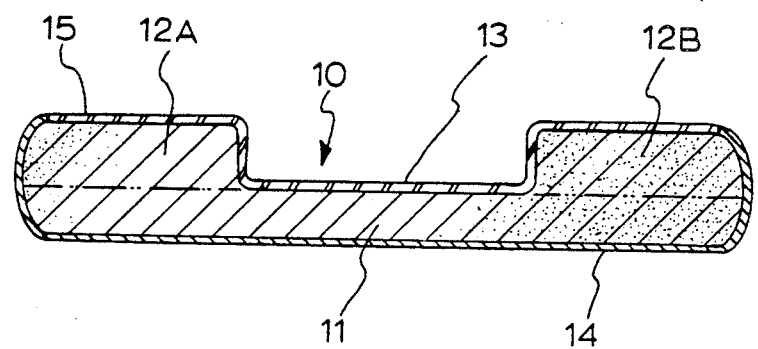
FIG. 2 is a vertical sectional view of the improved diaper shown in FIG. 1.

Referring to FIG. 2, numeral 14 denotes a water proof cover paper which covers the outside surface of the main body 11 and outside of each of the side walls 12A, 12B. Numeral 15 denotes a water permeable cover paper which covers the surface of the sink 13 and the top and the inside surfaces of each of the side walls 12A, 12B.

Figure 3:
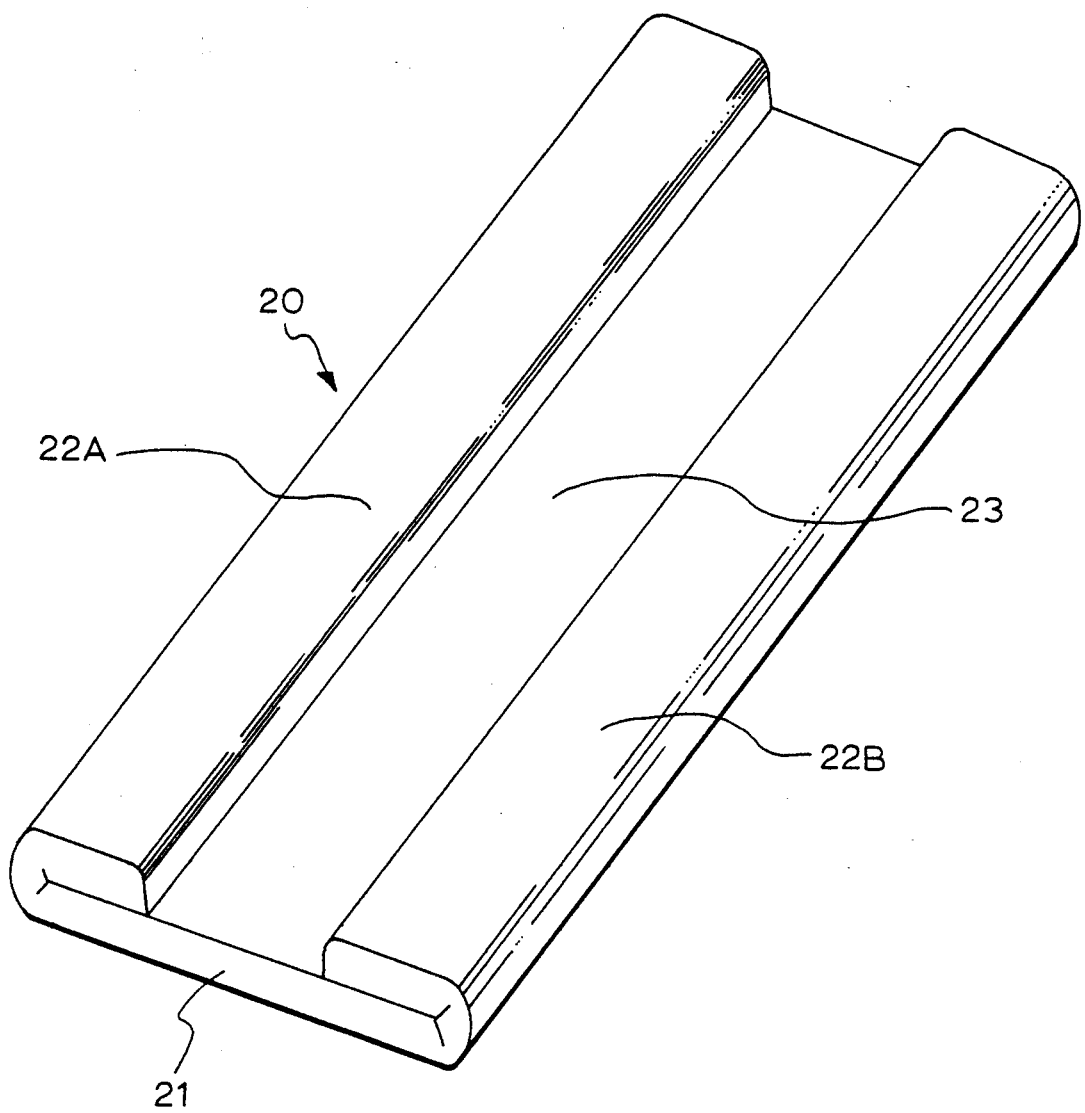
FIG. 3 is a perspective view of an improved diaper which is the second embodiment of the present invention.

FIG. 3 shows an improved diaper 20 which is the second embodiment of the present invention. In the second embodiment, a main body 21 of the diaper 20 is originally made in a wide flat rectangular form with predetermined dimensions, and side walls 22A, 22B are subsequently formed by folding the side sections of the main body 21 of its original wide flat form toward inside so that the side walls 22A, 22B are laid on the main body 21 and formed in a folded-over state as shown in FIG. 3. The folded-over side walls 22A, 22B are glued onto the unfolded parts of the main body 21 by an adhesive in only longitudinal end parts of the side walls 22A, 22B. In other words, longitudinally middle parts of the folded-over side walls 22, 22 are purposely left unglued.

With this construction, when the diaper 20 is applied to the body of the user in a U-shape, the unglued middle parts of the folded-over side walls 22A, 22B will partly unfold away from the the main body 21 and toward outside thereof. Thus, the height of the side walls 22A, 22B in their longitudinally middle parts will increase. The increased height of the side walls 22A, 22B will even more effectively prevent urine from spilling out of the diaper 20 sideways.

Figure 4:
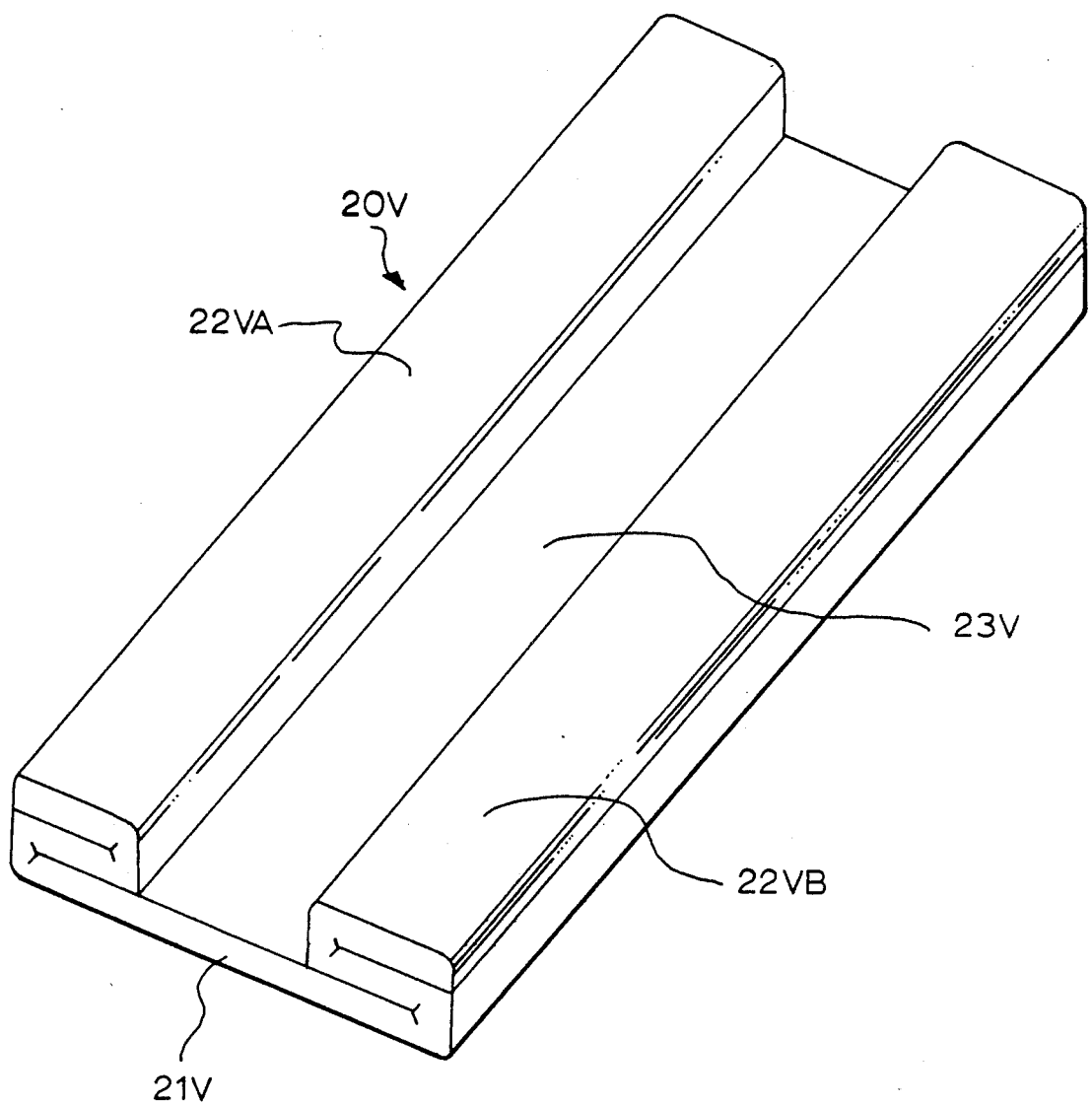
FIG. 4 is a perspective view of an improved diaper of the present invention which is a variation of the diaper shown in FIG. 3.

The diaper 20 of the second embodiment, as described above and shown in FIG. 3, have folded side walls 22A, 22B. FIG. 4 shows a diaper 20V which is a variation of the second embodiment. The side walls 22VA, 22VB of the diaper 20V are formed by first folding inward the side sections of the main body 21V of a wide flat original form and further folding back outward the one-half width of each of the folded-in parts to make two-fold side walls 22VA, 22VB, as shown in FIG. 4.

The diapers of the present invention, as described above, are simple in construction and easy to produce. In addition, they effectively prevent urine from spilling out sideways and can absorb all of the urine discharged.

Figure 5:
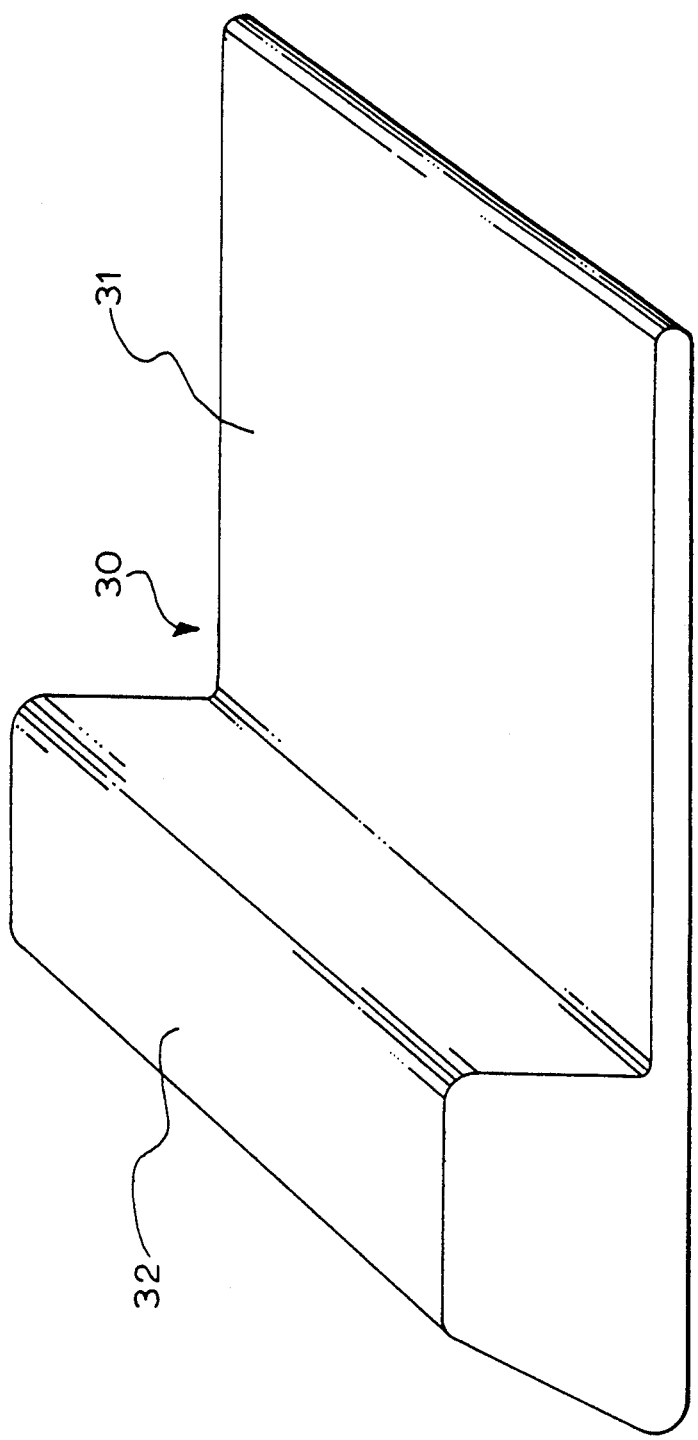
FIG. 5 is a perspective view of an improved diaper which is the third embodiment of the present invention.
Figure 6:
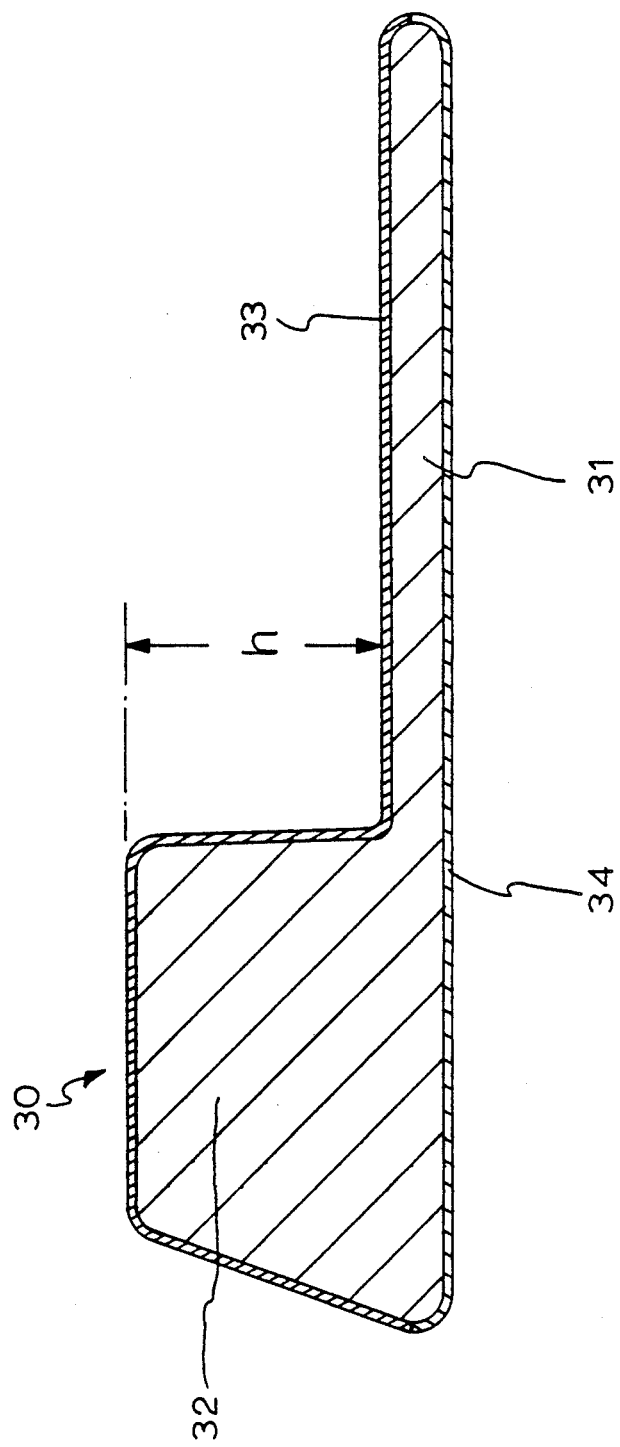
FIG. 6 is a vertical sectional view of the diaper shown in FIG. 5.

FIG. 5 shows an improved diaper 30 which is the third embodiment of the present invention. FIG. 6 shows a vertical sectional view of the diaper 30 shown in FIG. 5.

In FIG. 5, numeral 31 denotes a main body of the diaper 30. The main body 31 of the diaper 30 is made of a conventional soft, flexible paper material which may contain macromolecular water absorbent. Proper shape of the main body 31, for defecation of an adult person, is an approximate square having each side of 30 to 50 cm. The diaper 30 has a raised part 32 which is integrally formed with the main body 31 on one end thereof (i.e. on the end closer to the head of the diaper user) so that the buttocks of the user can be placed on the raised part 32 (the legs of the user come on the right-hand side as viewed in FIG. 5). The most effective height (denoted as "h" in FIG. 6) of the raised part 32 for an adult user is 5 to 10 cm. The height of the raised part 32 need not be limited to this range of dimension, however. The desirable configuration of the top surface of the raised part 32 is either flat or slightly convex.

Referring to FIG. 6, numeral 33 denotes a water permeable cover paper which covers the top surface of the main body 31 and the top surface and the side surfaces of the raised part 32. Numeral 34 denotes a water proof cover paper which covers the bottom surface of the main body 31.

Figure 7:
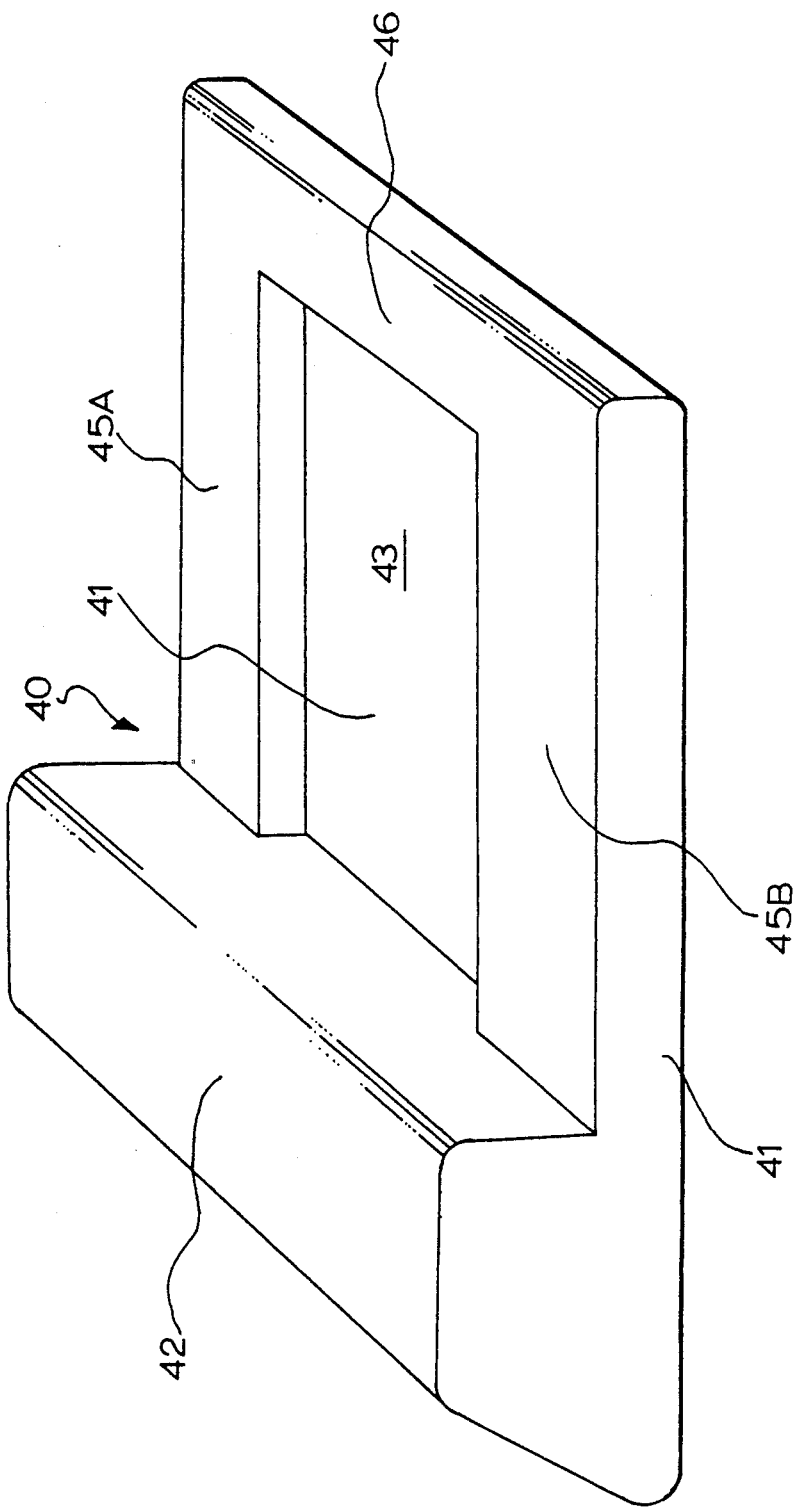
FIG. 7 is a perspective view of an improved diaper which is the fourth embodiment of the present invention.

FIG. 7 shows an improved diaper 40 which is the fourth embodiment of the present invention. The diaper 40 has a main body 41 and a raised part 42, in the same configuration and dimensions as those of the diaper 30 shown in FIGS. 5, 6, so that the buttocks of the user can be place thereon (the legs of the user come on the right-hand side as viewed in FIG. 7). The diaper 40 also has side walls 45A, 45B on the sides of main body 41, which are made integrally with the main body 41 so that discharged urine is kept from spilling out of the diaper 40 sideways. The proper height of the side walls 45A, 45B is 1 to 2 cm. The diaper 40 further has a end wall 46 which is formed on the front end (the furthest end from the head of the diaper user) section of the main body 41 and is made integrally with the main body 41 and the side walls 45A, 45B. Thus, the diaper 40 has a sink 43 on the main body 31, which is surrounded by the raised part 42, the side walls 45A, 45B and the end wall 46. Because the diaper 40 has such a configuration, it can be used by simply laying it flat under the buttocks or crotch area of the user without bending it in a U-shape like a conventional diaper. Because the end wall 46 and the side walls 45A, 45B keep the discharged urine from spilling out from the end section and the side sections, respectively, of the diaper 40, the urine remains in the sink 43 until it is completely absorbed into the material of the diaper 40. Because the raised part 42 holds the buttocks of the diaper, a sufficient space is provided between the anus and the surface of the diaper in which feces can remain without spreading and without spoiling the body of the diaper user.

Thus, the diaper 40, the fourth embodiment of the present invention, can keep all of discharged body excretions in the sink 43 on the main body 41 in the front (the leg side with respect to the position of the buttocks of the user) of the raised part 42 and at a lower level than the top level of the raised part 42. Therefore, the body of the user can be kept from being unnecessarily spoiled by the body excretions and the cleaning procedures after defecation are simple and easy. Furthermore, the diaper 40 is simply constructed and, therefore, the invention can be easily implemented.

What is claimed is:

1. A diaper having a three-dimensional configuration, made substantially of soft, flexible liquid absorbing material, comprising:
    (a) a main body formed in a substantially flat square shape having a top surface, a first side and a second side opposing each other, and a first end and a second end opposing each other;
    (b) a raised part for supporting thereon buttocks of a user of said diaper, said raised part being formed on said first end integrally with said main body;

(c) an end wall formed on said second end integrally with said main body, the height of said end wall being lower than the height of said raised part; and (d) a first side wall and a second side wall opposing each other, said first side wall being formed on said first side integrally with said main body and said second side wall being formed on said second side integrally with said main body so that said raised part, said end wall, said first side wall and said second side wall form a continuous four-sided wall integral with said main body, the height of each of said first and second side walls being lower than the height of said raised part and substantially equal to the height of said end wall.

* * * * *